United States Patent
Viola et al.

(10) Patent No.: US 11,702,314 B2
(45) Date of Patent: Jul. 18, 2023

(54) METHOD AND DEVICE FOR FEEDING ELASTIC THREADS IN A PLANT AND PROCESS FOR THE PRODUCTION OF LAYERED COMPOSITE ARTICLES

(71) Applicant: M.D. VIOLA MACCHINE S.R.L., Pavia (IT)

(72) Inventors: Marco Viola, Valle Salimbene (IT); Andrea Viola, Valle Salimbene (IT); Davide Viola, Valle Salimbene (IT)

(73) Assignee: M.D. VIOLA MACCHINE S.R.L., Pavia (IT)

( * ) Notice: Subject to any disclaimer, the term of this patent is extended or adjusted under 35 U.S.C. 154(b) by 297 days.

(21) Appl. No.: 17/293,394

(22) PCT Filed: Nov. 26, 2019

(86) PCT No.: PCT/IB2019/060160
§ 371 (c)(1),
(2) Date: May 12, 2021

(87) PCT Pub. No.: WO2020/121094
PCT Pub. Date: Jun. 18, 2020

(65) Prior Publication Data
US 2022/0009742 A1    Jan. 13, 2022

(30) Foreign Application Priority Data
Dec. 12, 2018   (IT) .......................... 102018000011037

(51) Int. Cl.
*B65H 59/38*   (2006.01)
*A61F 13/15*   (2006.01)
(Continued)

(52) U.S. Cl.
CPC ..... *B65H 59/388* (2013.01); *A61F 13/15593* (2013.01); *B65H 49/18* (2013.01);
(Continued)

(58) Field of Classification Search
CPC .... B65H 59/387; B65H 59/388; B65H 49/18; B65H 51/30; B65H 2701/319; B65H 2701/38; A61F 13/15593
See application file for complete search history.

(56) References Cited

U.S. PATENT DOCUMENTS 4,840,695 A   6/1989 Benim
5,525,175 A   6/1996 Blenke et al.
(Continued)

FOREIGN PATENT DOCUMENTS

EP    2 520 529 A1    11/2012
JP    H08-132576 A    5/1996

OTHER PUBLICATIONS

Mar. 10, 2020 International Search Report issued in International Patent Application No. PCT/IB2019/060160.
(Continued)

*Primary Examiner* — William E Dondero
(74) *Attorney, Agent, or Firm* — Oliff PLC

(57) ABSTRACT

A method for feeding elastic threads in a process for the production of layered composite articles includes: feeding at least one elastic thread along a path extending from a reel of an elastic thread up to a joining zone with at least one web material. Feeding the elastic thread along the above path includes: giving the elastic thread a first percentage elongation along a first section of the path extending between the reel and a control zone; giving the elastic thread a second percentage elongation along a second section of the path extending between the control zone and the joining zone. The second percentage elongation is greater than the first percentage elongation and a length of the first section is greater than a length of the second section.

14 Claims, 7 Drawing Sheets

(51) Int. Cl.
*B65H 49/18* (2006.01)
*B65H 51/30* (2006.01)

(52) U.S. Cl.
CPC ....... *B65H 51/30* (2013.01); *B65H 2701/319* (2013.01); *B65H 2701/38* (2013.01)

(56) References Cited

U.S. PATENT DOCUMENTS

| | | |
|---|---|---|
| 5,779,689 A | 7/1998 | Pfeifer et al. |
| 2011/0152811 A1 | 6/2011 | Bing-Wo et al. |
| 2014/0224855 A1 | 8/2014 | Smith |

OTHER PUBLICATIONS

Mar. 10, 2020 Written Opinion of the International Searching Authority issued in International Patent Application No. PCT/IB2019/060160.

FIG.4
FIG.5
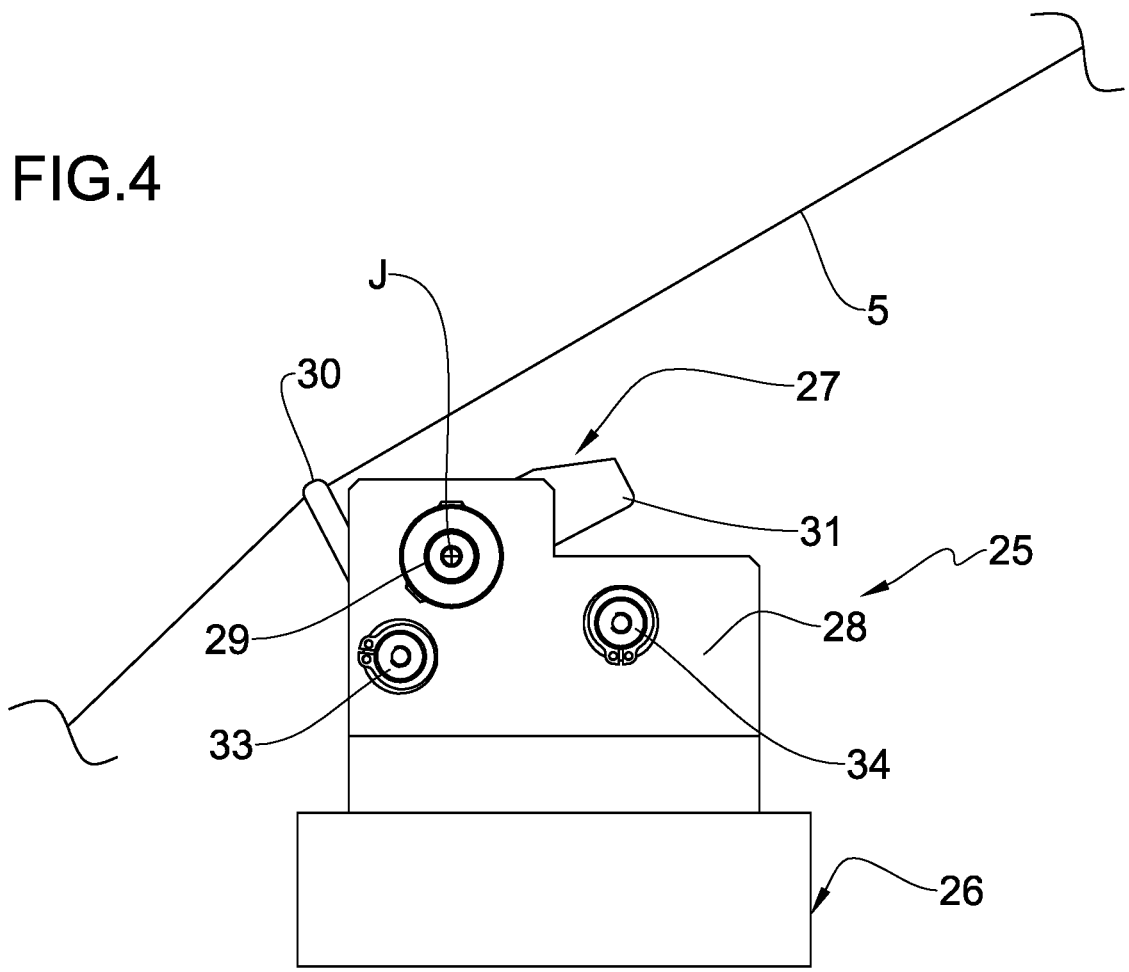
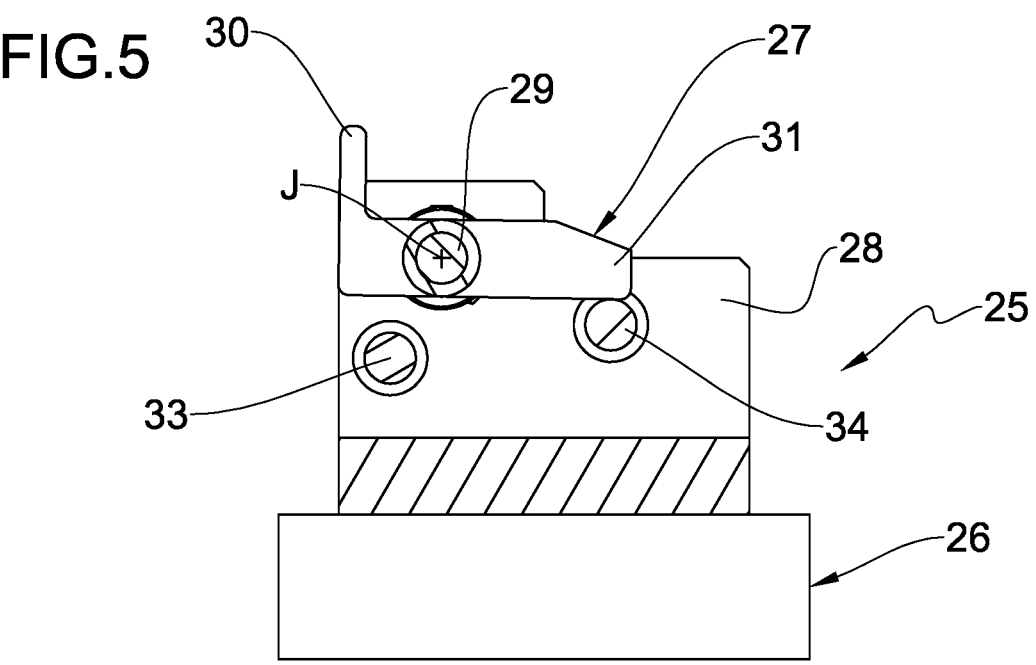

METHOD AND DEVICE FOR FEEDING ELASTIC THREADS IN A PLANT AND PROCESS FOR THE PRODUCTION OF LAYERED COMPOSITE ARTICLES

FIELD OF THE INVENTION

The present invention relates to a method and a device for feeding elastic threads in a plant and a manufacturing process for the production of layered composite articles. In particular, the present invention is part of the production of layered composite articles formed by sheets of fabric and/or non-woven fabric (TNT) and any other elements such as to give the articles the desired properties (such as: impermeability, absorption, breathability, elasticity, etc.). The elastic threads serve to give the desired elasticity to said articles or parts of them. Such articles may for example be articles of clothing. Preferably but not exclusively, the present invention is part of the production lines of sanitary articles, such as sanitary napkins, diapers, diapers for adults, panty liners, etc., whose manufacturing is performed starting from different semi-finished products, among which web materials wound in reels, such as, for example, polyethylene, non-woven fabric, cellulose wadding (tissue) and elastic threads (for example formed by polyurethane fibers) also wound in reels.

Prior Art

In the production lines of sanitary items, the web materials are unwound from the respective reels to be subsequently fed to processing stations which provide for example to combine them with other materials, cut them to size, etc.

For example, it is known to convey two webs and a plurality of elastic threads through a pair of counter-rotating rollers, so as to glue the elastic threads and arrange them between the two webs before entering through the rollers and thus form an elastic semi-finished product consisting of said two webs and of the elastic threads interposed at the outlet of said two rollers. The elastic threads are also kept in traction so as to give the semi-finished product and the finished articles the desired elastic properties. The percentage elongation necessary to obtain these elastic properties of the finished article can be close to the elongation at break of the elastic thread, which for polyurethane fibers can be for example between 200% and 800%.

In today's production lines, in which the number of webs, elastic threads and other components handled and processed is continuously increasing to produce increasingly complex articles, the number and bulk of the elastic thread reels is such as to have to arrange them far from the joining zone to the webs.

Public document EP 2 520 529 illustrates a device for feeding elastic yarns comprising a tension control system, configured to control the tension of the elastic yarn coming from a reel, and a motor roller, configured to feed the elastic yarn coming from the tension control system to a processing line.

Public document US 2011/152811 discloses a method for manufacturing an extensible article, such as a diaper, provided with at least one polymeric extensible yarn, and a system configured to glue the yarn between layers of the extensible article.

Public document U.S. Pat. No. 5,525,175 illustrates an apparatus and a method for applying an elastic thread on a substrate moving along a curved path.

Public document U.S. Pat. No. 4,840,695 illustrates a method and an apparatus for unwinding web of elastic material.

OBJECT OF THE INVENTION

The Applicant has noticed that the elastic threads must travel over a very long path and for a long transit time before being coupled to the webs and possibly to other elements. For example, the path of the elastic threads from the reels to the counter-rotating rollers may even be dozens of meters for a transit time of a few seconds during which the elastic threads undergo the aforementioned percentage elongation close to their breaking point.

The Applicant has observed that the high stresses (in terms of value and time) to which the elastic threads are subjected very frequently cause their breakage with consequent machine downtime necessary to repair the thread and therefore loss of line productivity.

Moreover, the Applicant has noticed that the remote location (sometimes above the production line) of the elastic thread reels is such as to make the intervention of the operators (who must inspect the entire path of the thread to find the breaking point) long and complex in the event of breakage, with consequent further loss of line productivity.

In this context, the Applicant has therefore set himself the object of proposing a method and a device for feeding elastic threads in a plant for the production of layered composite articles which allow first of all eliminating or at least drastically reducing the breakages of the elastic threads along the paths that take them from the reels to the joining zone(s) with other elements of the articles in production.

The Applicant has also set itself the object of proposing a method for feeding elastic threads which can be implemented with simplicity and which does not require significant variations in the production steps of the production lines.

The Applicant has also set itself the object of proposing a device for feeding elastic threads which can be easily integrated into existing production lines without requiring drastic changes thereof.

The Applicant has also set itself the object of proposing a device for feeding elastic threads which is structurally simple, cost-effective and easy to manage and maintain.

SUMMARY OF THE INVENTION

The Applicant has found that such objects and further tasks can be obtained by implementing a method and a device according to the present invention, of the type claimed in the appended claims and/or described in the following aspects.

In particular, the Applicant has found that such objects and further tasks can be obtained by transporting the elastic threads from the respective reels up to the proximity of the joining zone (to the web materials and/or to other elements) with an elongation/tension far from their breaking point to then give them the tension/elongation required for joining to the web materials only in a last short section placed immediately upstream of said joining zone.

In particular, according to a first aspect, the present invention relates to a method for feeding elastic threads in a process for the production of layered composite articles.

The method comprises: feeding at least one elastic thread along a path extending from a reel of said elastic thread up to a joining zone with at least one web material, wherein feeding said at least one elastic thread along said path comprises:

giving said at least one elastic thread a first percentage elongation along a first section of said path extending between the reel and a control zone;

giving said at least one elastic thread a second percentage elongation along a second section of said path extending between the control zone and the joining zone;

wherein the second percentage elongation is greater than the first percentage elongation. Optionally, a length of the first section is greater than a length of the second section.

According to a second aspect, the present invention relates to a device for feeding elastic threads in a plant for the production of layered composite articles. The device comprises: at least one reel holder for at least one elastic thread wound on a reel and at least one motorized unwinding roller associated with the reel holder; a pair of opposed transport surfaces configured to receive each other and to join at least one web material with said at least one elastic thread unwound from the reel; a control device comprising at least one motorized transport surface; wherein the motorized transport surface is operatively arranged between the motorized unwinding roller and the pair of opposed transport surfaces to act on the elastic thread extending between the motorized unwinding roller and the pair of opposed transport surfaces.

The control device is configured and/or programmed to adjust a linear speed of the motorized transport surface so as to give said at least one elastic thread a first percentage elongation, between the motorized unwinding roller and the control device, less than a second percentage elongation, between the control device and the pair of opposed transport surfaces.

The second percentage elongation is meant as the sum of the first percentage elongation and a further additional percentage elongation determined by the action of the control device and of the pair of opposed transport surfaces. With the additional percentage elongation, a further tension is added to the tension already imparted by the first percentage elongation.

The device is configured to define a path for the elastic thread and such a path extends between the reel holder and the pair of opposed transport surfaces. Said path comprises a first section extending between the reel holder and the control device and a second section which extends between the control device and the pair of opposed transport surfaces. The first section of said path is greater than the second section of said path.

According to an aspect, the present invention relates to a process for the production of layered composite articles, comprising:

feeding web materials (such as, for example, polyethylene, non-woven fabric, cellulose wadding) along respective paths;

associating and joining together said web materials and possibly further elements to form a continuous semi-finished product;

cutting said continuous semi-finished product to form layered composite articles;

wherein the process also comprises the method according to the first aspect and/or to one or more of the following aspects.

According to an aspect, the present invention relates to a plant for the production of layered composite articles, comprising:

a plurality of reel holders for respective reels of web materials (such as, for example, polyethylene, non-woven fabric, cellulose wadding);

a plurality of transport and return devices defining respective paths for said web materials;

a plurality of joining devices acting along said paths for joining said web materials and possible further elements together and forming a continuous semi-finished product;

at least one cutting device for cutting said continuous semi-finished product and forming layered composite articles;

at least one device for feeding elastic threads according to the second aspect and/or to one or more of the following aspects.

The Applicant has verified that the solution according to the invention allows first of all increasing the productivity of the plants and processes for the production of layered articles due to the elimination, or at least the considerable reduction, of the breakages of the elastic threads during production.

The Applicant has in fact verified that the reduction in the percentage elongation of the elastic threads in the longest section of their path ensures that in such a section there can be no breakages.

The Applicant has also verified that the concentration of the greater percentage elongation in the short section (in terms of space and time) placed immediately before the junction with the web material(s) allows eliminating or reducing the breakages also in such a short section, since the threads are kept at a high percentage elongation only for fractions of a second.

The Applicant has also verified that the possible and rare breakages occur only in this last short section and can be easily located and repaired by the operators.

The Applicant has therefore verified that the solution according to the invention allows improving the quality of the layered articles produced, in particular of their elastic parts, since they contain elastic threads which have been little stressed during production.

Further aspects of the invention are described below.

In one aspect, the layered composite articles are sanitary articles, such as but not exclusively: sanitary napkins, diapers, diapers for adults, panty liners.

In one aspect, the layered composite articles are clothing or accessories.

In one aspect, said method allows making elastic portions of said layered composite articles.

In one aspect, said at least one elastic thread comprises or is formed by synthetic fibers, optionally of polyurethane, for example known by the names of Lycra®, Spandex, Elastam.

In one aspect, said at least one elastic thread has a percentage elongation at break greater than or equal to 200%, optionally greater than or equal to 400%.

In one aspect, said at least one elastic thread has a percentage elongation at break less than or equal to 800%, optionally less than or equal to 600%.

In one aspect, it is provided to feed a plurality of parallel elastic threads.

In one aspect, the elastic threads fed in parallel are at least ten, optionally at least twenty, more optionally a few dozens, optionally for each elastic portion to be manufactured.

In one aspect, each of the elastic threads is wound on a respective reel.

In one aspect, a plurality of reel holders carries the plurality of reels.

In one aspect, several reels are associated with a motorized unwinding roller.

In one aspect, the motorized unwinding roller lies in contact with the reel and rotates it, unwinding the elastic thread.

In one aspect, a plurality of motorized unwinding rollers is provided, each associated with at least one reel or reel holder, optionally to a plurality of reels or reel holders.

In one aspect, on said pair of opposed transport surfaces, the web material and said at least one elastic thread, optionally the plurality of parallel elastic threads, advance in parallel.

In one aspect, two web materials pass between the pair of opposed transport surfaces and said at least one elastic thread, optionally the parallel elastic threads, are inserted between the two web materials.

In one aspect, at least one of the opposed transport surfaces is motorized.

In one aspect, an adhesive is deposited on the elastic thread(s) and/or on the web material(s) before the elastic thread(s) and web materials(s) pass between the pair of opposed transport surfaces.

In one aspect, feeding said at least one elastic thread along said path comprises: imparting to the elastic thread a first linear speed at the respective reel, optionally at and by means of the motorized unwinding roller.

In one aspect, the first linear speed is a peripheral speed of the motorized unwinding roller.

In one aspect, feeding said at least one elastic thread along said path comprises: imparting to the elastic thread a second linear speed at the control zone, optionally at and by means of the motorized transport surface of the control device.

In one aspect, the second linear speed is a speed of the motorized transport surface.

In one aspect, feeding said at least one elastic thread along said path comprises: imparting to the elastic thread and to the web(s) a third linear speed at the joining zone, at and by means of the pair of opposed transport surfaces.

In one aspect, the third linear speed is a speed of the pair of opposed transport surfaces.

In one aspect, the second linear speed is greater than the first linear speed.

In one aspect, the second linear speed is less than the third linear speed.

In one aspect, a ratio between the second linear speed and the first linear speed is between 1.01 and 4, optionally between 2 and 4.

In one aspect, a ratio between the third linear speed and the second linear speed is between 5 and 9.

In one aspect, the control device comprises a first roller and a second roller having reciprocally coupled peripheral surfaces and defining said at least one motorized transport surface.

In one aspect, at least one of said first roller and second roller is motorized.

In one aspect, an actuator or weight presses the first roller against the second roller.

In one aspect, the peripheral surface of the first roller is metallic and the peripheral surface of the second roller is made of a material with a high sliding friction coefficient, such as rubber, or vice versa.

In one aspect, said at least one elastic thread passes between the first roller and the second roller and lies in contact with the peripheral surface of the first roller and with the peripheral surface of the second roller.

The Applicant has verified that, if an elastic thread breaks in the second section, the control device is able to hold it between said first roller and second roller and to make it very simple for the operator to identify and repair it.

In one aspect, a pair of counter-rotating rollers, of which at least one is motorized, defines the pair of opposed transport surfaces. In particular, peripheral surfaces of the rollers of the pair define, in the mutual contact zone, said opposed transport surfaces.

In one aspect, a ratio between the first percentage elongation and the second percentage elongation is greater than or equal to 0.1, optionally greater than or equal to 0.5.

In one aspect, a ratio between the first percentage elongation and the second percentage elongation is less than or equal to 0.9, optionally less than or equal to 0.7.

In one aspect, a ratio between the first percentage elongation and a percentage elongation at break of said elastic thread is less than 0.4, optionally less than 0.1. In this way, the thread(s) is/are little stressed in the longest section.

In one aspect, a ratio between the second percentage elongation and a percentage elongation at break of said elastic thread is less than 0.8, optionally less than 0.6.

In this way, the thread(s) is/are stressed for the short second stretch only.

In one aspect, the first percentage elongation is just sufficient to allow the unwinding of the thread from the reel.

In one aspect, the first percentage elongation is less than or equal to 300%, optionally between 1% and 300%, more optionally between 100% and 300%.

In one aspect, the second percentage elongation is greater than or equal to 400%, optionally between 400% and 800%.

In one aspect, a ratio between the length of the second section and the length of the first section is greater than or equal to 0.02, optionally greater than or equal to 0.05.

In one aspect, a ratio between the length of the second section and the length of the first section is less than or equal to 0.5, optionally less than or equal to 0.2.

In one aspect, the length of the second section is less than 1 m, optionally less than 0.5 m.

In one aspect, the length of the first section is greater than 2 m, optionally greater than 5 m, more optionally greater than 10 m.

In one aspect, an electronic control unit is operatively connected to the control device and is configured and/or programmed to adjust a linear speed (second linear speed) of the motorized transport surface.

In one aspect, the electronic control unit is operatively connected to the control device and is configured and/or programmed to adjust the rotation speed of the first roller and of the second roller.

In one aspect, the electronic control unit is configured and/or programmed to adjust a linear speed (second linear speed) of the motorized transport surface as a function of a linear speed (third linear speed) of the pair of opposed transport surfaces.

In one aspect, the electronic control unit is configured and/or programmed to adjust a linear speed (first linear speed) of the unwinding roller or of the reel according to a linear speed (second linear speed) of the motorized transport surface.

In one aspect, a first load cell is located just downstream of the reel of elastic thread and operatively coupled to each elastic thread to measure a tension correlated to the first percentage elongation and a second load cell is located just downstream of the control device and operatively coupled to each elastic thread to measure a tension correlated to the second percentage elongation.

In one aspect, the electronic control unit is configured and/or programmed to adjust a linear speed (first linear speed) of the unwinding roller and/or a linear speed (second linear speed) of the motorized transport surface according to the tensions detected by the load cells, so as to give each elastic thread said first percentage elongation and said second percentage elongation.

In one aspect, the ratio between the second linear speed and the first linear speed is set by dimensioning the unwinding roller and the first roller and the second roller.

In one aspect, the ratio between the third linear speed and the second linear speed is set by dimensioning the first roller and the second roller.

In one aspect, a device for signaling the breakage of threads in a plant for the production of layered composite articles is operatively positioned between the control device and the pair of opposed transport surfaces.

The device for signaling is located in the section where the breakages are concentrated. These rare breakages can therefore be even more easily located and repaired by the operators.

The device for signaling comprises: a support body; a series/plurality of rocker arms mounted on the support body, mutually juxtaposed and oscillating about a common axis.

Each of the rocker arms comprises a head end, configured to come into contact with a respective stretched thread of a plurality of threads passing over said rocker arms, and a tail end opposite the head end.

Each of the rocker arms is movable around the common axis independently of the other rocker arms between a first position, in which the head end is lowered by the action of the stretched thread acting on said head end, and a second position, in which the head end is raised in the absence of said stretched thread and under the action of the weight of the rocker arm acting on a center of mass placed between the common axis and the tail end.

The Applicant has verified that for the operator it is immediate to visually perceive the breakage of a thread and identify it thanks to the head end of the rocker arm which protrudes from the set/plurality of rocker arms.

In one aspect, the signaling device comprises an electrical circuit.

In one aspect, in the second position, each of the rocker arms closes or opens a contact of said circuit.

In one aspect, in the second position, each of the rocker arms triggers an alarm signal.

In one aspect, in the second position, each of the rocker arms triggers a signal to stop the plant or at least part of said plant.

By the adjective "motorized" used above, it is meant that the unwinding roller, the transport surface and said at least one of the opposed transport surfaces is each connected to and moved by a respective motor or by/to a motor common to several elements, for example through a transmission.

Further features and advantages will become more apparent from the detailed description of a preferred but non-exclusive embodiment of a method and a device for feeding elastic threads in a plant and process for the production of layered composite articles according to the present invention.

BRIEF DESCRIPTION OF THE DRAWINGS

Such description is given hereinafter with reference to the accompanying drawings, provided only for illustrative and, therefore, non-limiting purposes, in which:

FIG. 4 is an enlarged lateral view of an element being part of the device of FIG. 2;

FIG. 5 is a lateral sectional view of the element of FIG. 4;

DETAILED DESCRIPTION OF PREFERRED EMBODIMENTS OF THE INVENTION

Figure 1:
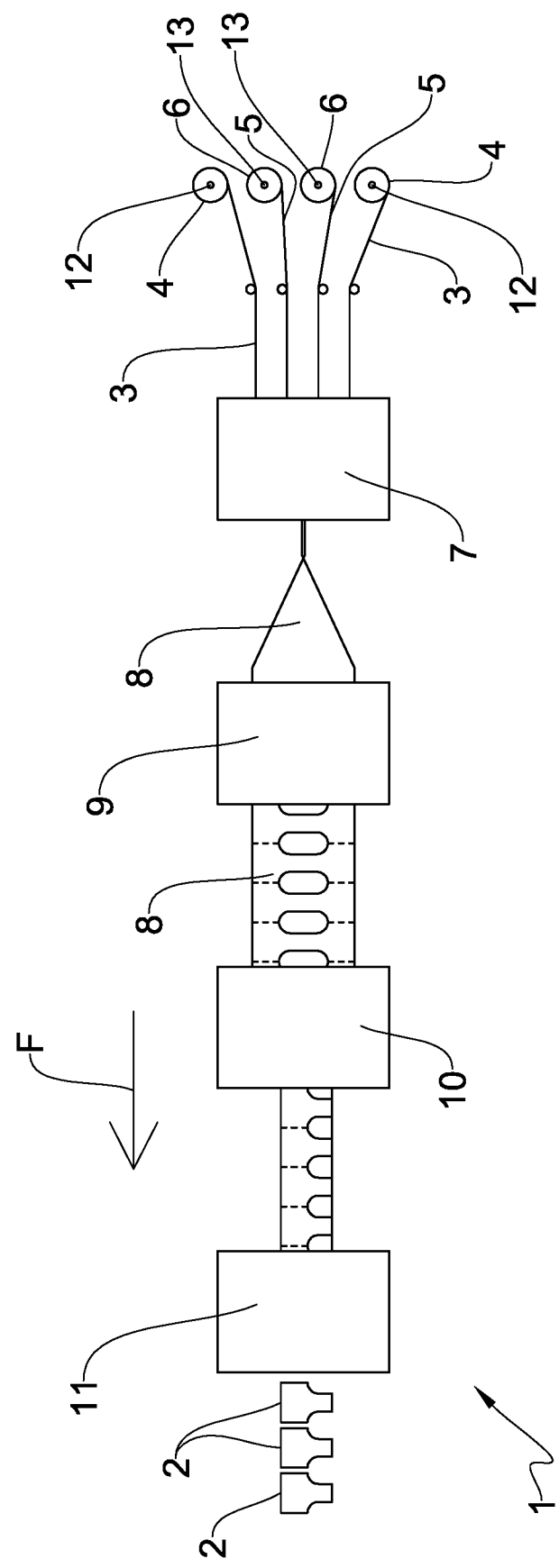
FIG. 1 shows a schematic view of a plant for the production of layered composite articles according to the present invention.

With reference to the accompanying figures, with reference numeral 1 a manufacturing plant for the production of layered composite articles 2 has been generally indicated. The plant 1, illustrated as a preferred example, is configured to produce diapers 2. In other embodiments not shown, the plant 1 may be configured to produce other types of hygienic-sanitary articles 2, such as for example: sanitary napkins, diapers for adults, panty liners. In other embodiments not shown, the plant 1 may be configured to produce clothing or accessories.

In the plant 1, the manufacturing of the above articles 2 is carried out starting from different semi-finished products, among which web materials 3 wound in reels 4, such as for example polyethylene, non-woven fabric, cellulose wadding (tissue), and threads 5 wound in reels 6, such as for example elastic threads formed by synthetic fibers, optionally polyurethane (for example known by the names of Lycra®, Spandex, Elastam).

The web materials 3 and the threads 5 are fed continuously through the plant 1 along respective paths and are joined, molded, and cut, etc., to give rise to the above articles 2. In the schematic example shown in FIG. 1, the plant 1 comprises a first sector 7 along which the web materials 3 and the threads 5 are joined together to form a continuous semi-finished product 8 fed along a transport direction "F". The semi-finished product 8 is rotated by 90° as it advances towards a second sector 9 in which it is cut/shaped. In a third sector 10, the semi-finished product 8 is folded in two along a longitudinal line and therefore, in a fourth sector 11, weldings are made and the individual articles/diapers 2 are separated from each other.

The plant 1 comprises a plurality of reel holders 12 for the respective reels 4 of web materials 3, a plurality of reel holders 13 for the respective reels 6 of elastic threads 5. The first sector 7 is provided with transport and return devices which define respective paths for said web materials 3 and for the elastic threads 5, and devices for joining/gluing acting along said paths to join together said web materials 3 with the elastic threads 5 and with further elements and form the continuous semi-finished product 8. The second sector 9 comprises transport and return devices for the continuous semi-finished product 8 and cutting and shaping devices. The third sector 10 also comprises transport and return devices and cutting and welding devices. The fourth sector 11 comprises at least one cutting device configured to cut said continuous semi-finished product 8 and separate the layered composite articles 2 (diapers).

In the first sector 7, in order to make elastic portions of the above diapers 2 (for example, placed at the waist and/or at the openings for the legs), a plurality of said parallel elastic threads 5 are inserted between and joined to a pair of web materials 3, to form an elastic semi-finished web product 14 consisting of the two web materials 3 between which the elastic threads 5 (FIGS. 2 and 3) are glued.

Figure 2:
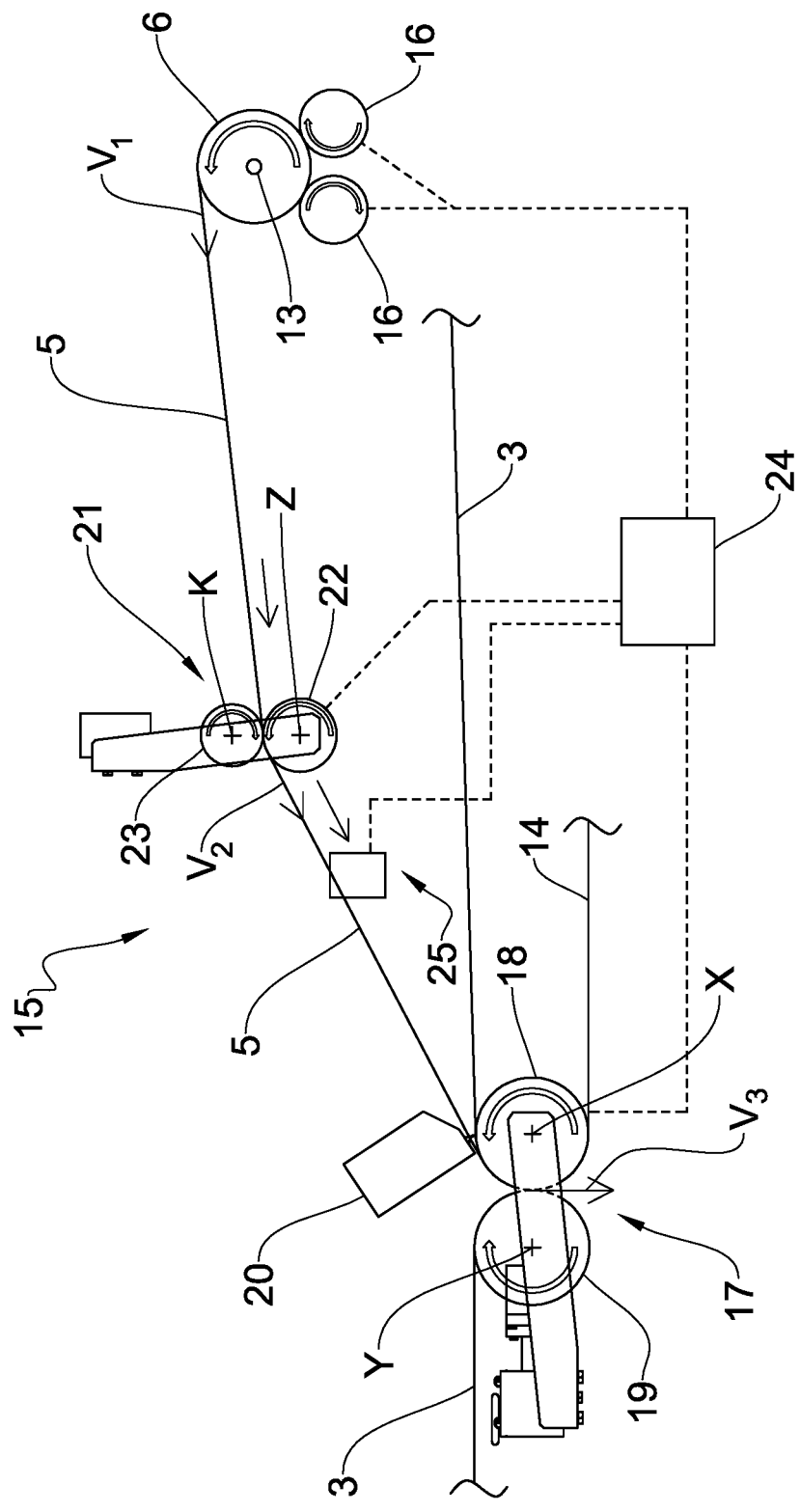
FIG. 2 shows a device for feeding threads according to the present invention and forming part of the plant of FIG. 1.

For this purpose, the first sector 7 is provided with a device 15 for feeding the elastic threads 5 and joining them to the web material(s) 3 (FIG. 2).

This device 15 for feeding the elastic threads 5 comprises the above reel holders 13 coupled to two motorized unwinding rollers 16. In the illustrated embodiment, the reels 6 of the elastic threads 5 rest on the two motorized unwinding rollers 16. The two motorized unwinding rollers 16 are made to rotate, by means of at least one motor connected to them and not shown, in synchronous directions and determine the rotation of the reels 6 in the opposed direction and the unwinding of the respective elastic threads 5. The elastic threads fed in parallel are a few dozen. In the illustrated embodiment, the elastic threads are twenty-five.

Several reels 6 are arranged side by side and associated with a pair of motorized unwinding rollers 16. FIG. 2 shows only one reel 6 because the others are hidden behind such a reel 6. There may also be more pairs of motorized unwinding rollers 16 (although only one is shown in FIG. 2) and each pair of motorized unwinding rollers 16 is associated with a plurality of reels 6 arranged side by side.

Figure 3:
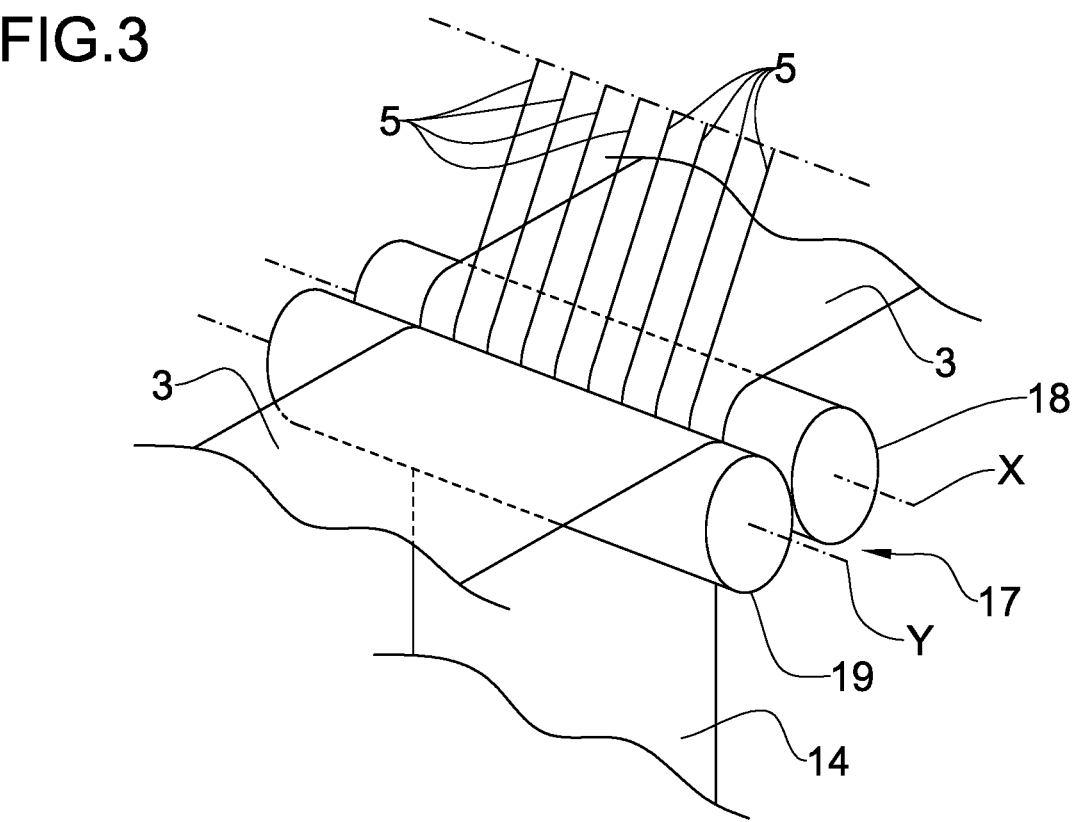
FIG. 3 shows a perspective view of some elements of the device of FIG. 2.
Figure 6:
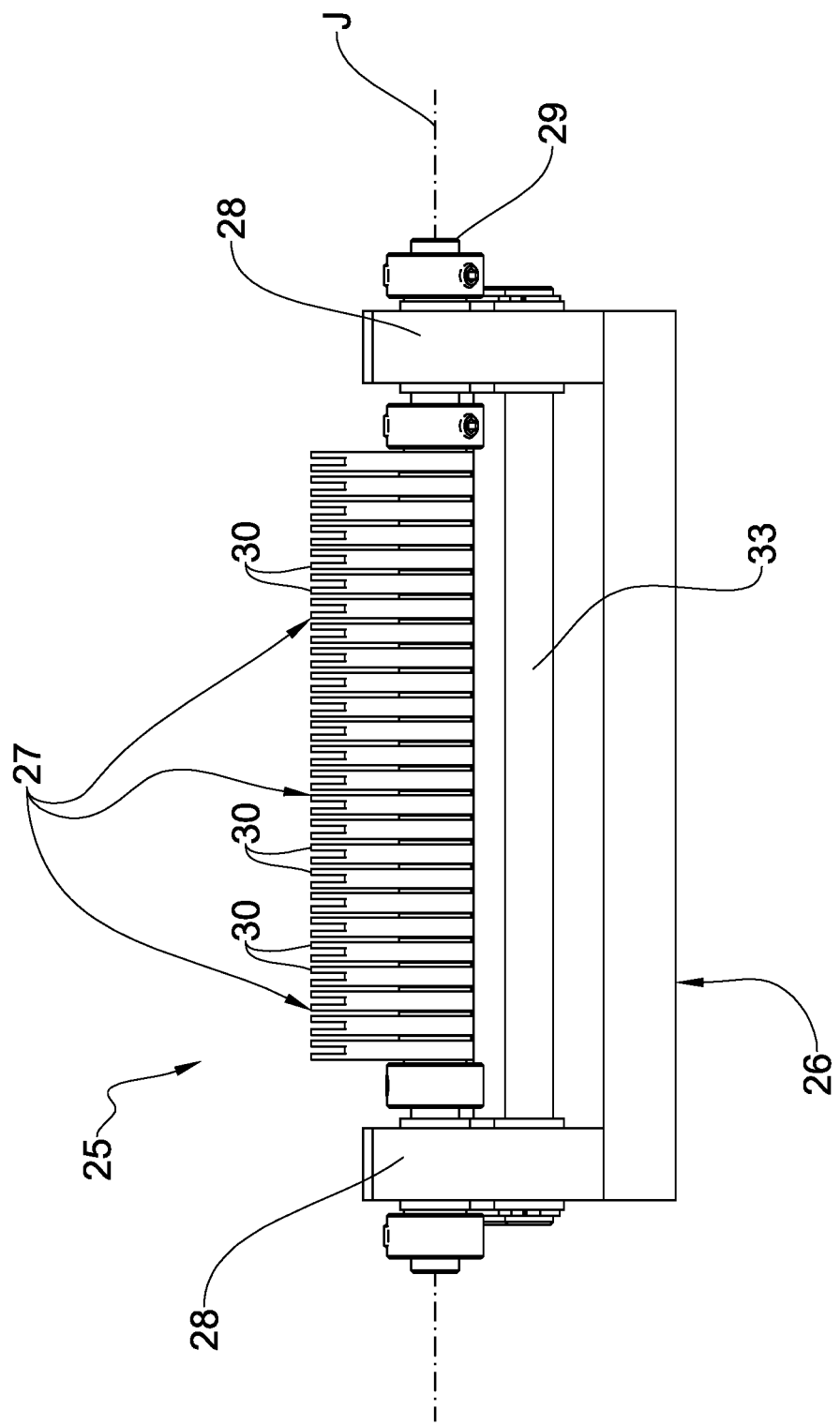
FIG. 6 is a front view of the element of FIGS. 4 and 5.
Figure 7:
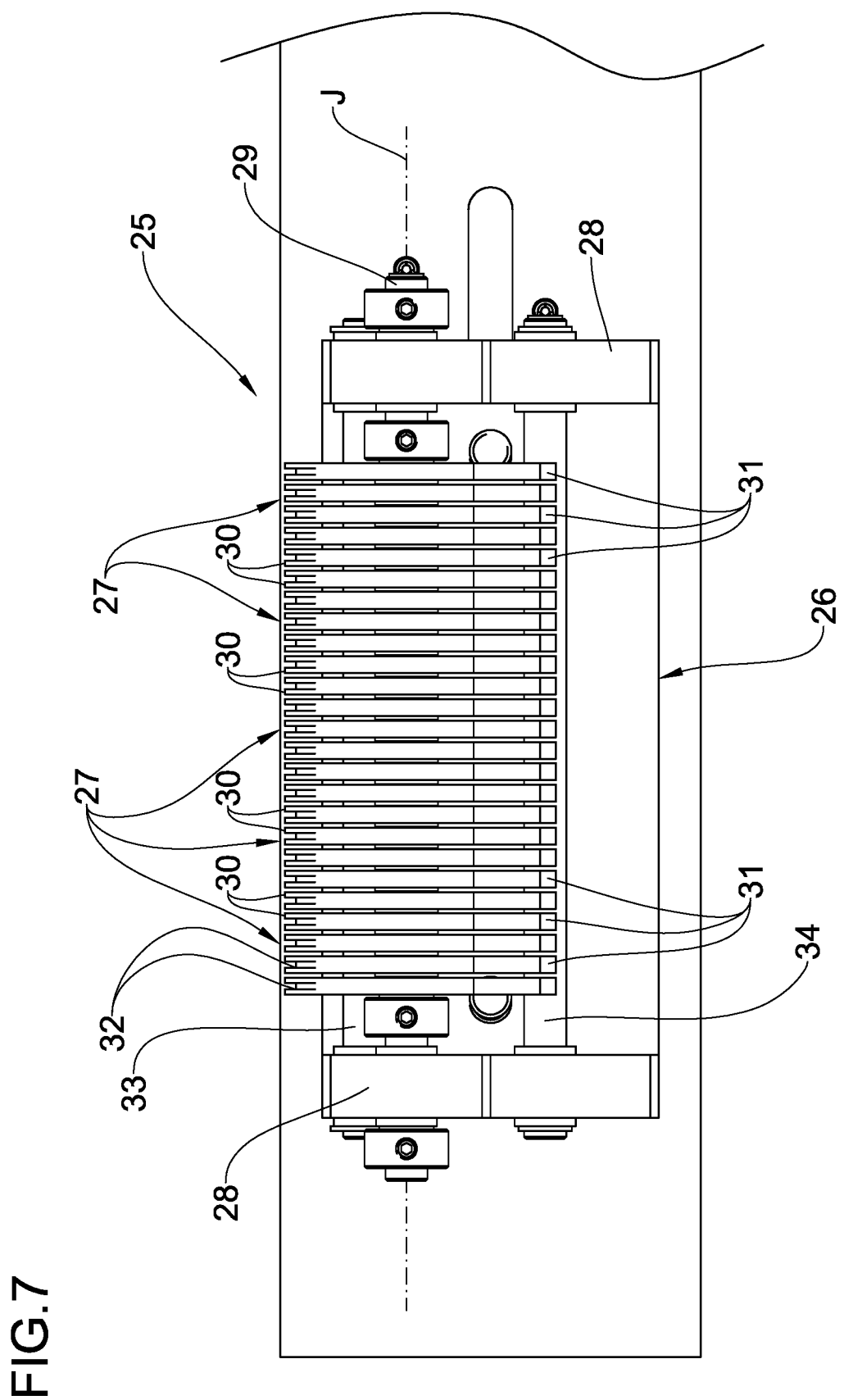
FIG. 7 is top view of the element of FIGS. 4, 5 and 6.

The elastic threads 5 coming from the reels 6 are fed along parallel paths lying in a same plane, as illustrated in FIG. 3. In FIGS. 2 and 4 only one thread 5 is visible because the others are hidden behind such a thread 5.

The device 15 for feeding the elastic threads 5 also comprises a pair of counter-rotating rollers 17. A main roller 18 of the pair 17 is motorized, i.e. it is connected to a motor, not shown, which causes it to rotate about a first axis "X" thereof. An auxiliary roller 19 of the pair 17 is driven by the main roller 18 around a second axis "Y" parallel to the first axis "X". The peripheral surfaces of the rollers 18, 19 of the pair 17 are mutually juxtaposed and constitute, in a zone of mutual contact, a pair of opposed transport surfaces.

The opposed transport surfaces are configured to receive between them and join the parallel elastic threads 5 with the pair of web materials 3 while the threads 5 and the web materials 3 move parallel between said opposed transport surfaces. The pair of counter-rotating rollers 17 therefore defines a zone for joining the threads 5 with the web materials 3.

For this purpose, a glue dispenser 20 is positioned above the pair of counter-rotating rollers 17 to intercept the elastic threads 5 and deposit adhesive on them before they come into contact with the web materials 3.

The device 15 is configured to define a path for the elastic threads 5 and such a path extends between the reels 6 (or the reel holders 13) and the pair of opposed transport surfaces defined by the rollers 18, 19.

A control device 21 is arranged between the two motorized unwinding rollers 16 and the pair of counter-rotating rollers 17 and along the path of the elastic threads 5, so as to intercept said elastic threads 5 (FIG. 2). The path of the elastic threads 5 comprises a first section extending between the reels 6 (or the reel holders 13) and the control device 21 and a second section which extends between the control device 21 and the pair of opposed transport surfaces. The first section of said path is greater than the second section of said path.

The control device 21 comprises a first roller 22 and a second roller 23 having reciprocally coupled peripheral surfaces and defining motorized transport surfaces. In the illustrated embodiment, the first roller 22 or lower roller is motorized, i.e. it is connected to a motor, not shown, which causes it to rotate about a first axis "Z" thereof, while the second roller 23 or upper roller is driven in rotation by the first roller 22 around a respective second axis "K".

The first and second axis "X", "Y" of the pair of counter-rotating rollers 17 and the first and second axis "Z", "K" of the control device 21 are parallel to each other. The peripheral surface of the first roller 22 is metallic and the peripheral surface of the second roller 23 is made of a material with a high sliding friction coefficient, such as rubber or silicone, and an actuator or weight presses the first roller 22 against the second roller 23. The parallel elastic threads 5 pass between the first roller 22 and the second roller 23 and are wound around by a circumference arc of about 20° about the first roller 22.

The control device 21 is configured and/or programmed to adjust a linear speed of its motorized transport surfaces, so as to give the elastic threads 5 a first percentage elongation, along the first section which extends between the motorized unwinding rollers 16 or the reels 6 and the control device 21, less than a second percentage elongation, along the second section which extends between the control device 21 and the pair of counter-rotating rollers 17.

The control device 21 is positioned in the vicinity of the pair of counter-rotating rollers 17, so as to minimize the length of the second section and the time during which the threads 5 are subjected to the greatest elongation, necessary to obtain the desired elastic features of the elastic semi-finished web product 14.

For example, the length of the first section is greater than 10 m while the length of the second section is about 1 m. For example, a ratio between the length of the second section and the length of the first section is equal to about 0.1.

For this purpose, an electronic control unit 24, schematically illustrated in FIG. 2, is operatively connected to the control device 21, to the motorized unwinding rollers 16 and to the pair of counter-rotating rollers 17, to adjust the relative speeds thereof.

The electronic control unit 24 is configured to adjust the ratios between:

a first linear speed "V1" of the unwinding rollers 16 or of the reels 6 (peripheral speed of the unwinding rollers 16 or of the reels 6 which correspond to the speed of the threads 5 which unwind from the reels 6 themselves);

a second linear speed "V2" of the first roller 22 and of the second roller 23 (peripheral speed of said first roller 22 and second roller 23 which corresponds to the speed of the threads 5 in the contact points with said rollers 22, 23);

a third linear speed "V3" of the pair of opposed transport surfaces (peripheral speed of the main roller 18 and of the auxiliary roller 19 of the pair 17 of counter-rotating rollers which corresponds to the speed of the threads 5 and of the web materials 3 in the contact points with said rollers 18, 19).

To keep the first percentage elongation smaller than the second percentage elongation, the second linear speed "V2" is greater than the first linear speed "V1" and less than the third linear speed "V3".

For example, for elastic threads 5 in polyurethane fibers (Lycra®, Spandex, Elastam) which have a percentage elongation at break equal to about 500%, a ratio between the second linear speed "V2" and the first linear speed "V1" is kept equal to about three and a ratio between the third linear speed "V3" and the second linear speed "V2" is kept equal to about five.

In this way, the first percentage elongation of the elastic threads 5 along the first section is equal to about 200% and the second percentage elongation of the elastic threads 5 along the second section is equal to about 400%. A ratio between the first percentage elongation and the second percentage elongation is equal to about 0.5 and a ratio between the first percentage elongation and the percentage elongation at break of said elastic thread is equal to about 0.4. A ratio between the second percentage elongation and the percentage elongation at break of said elastic thread is equal to about 0.8.

In this way, the elastic threads 5 are not very stressed along the first transport portion which from the reels 6 leads to the control device 21 and are subjected to high tensile stresses (necessary to correctly couple the threads 5 to the web materials 3 and obtain the desired elastic properties) only in the short second section. The possible breakages of the threads 5 are therefore concentrated in the second section and, if an elastic thread 5 breaks in said second section, the control device 21 is able to hold it between said first roller and second roller 22, 23 (of rubber or silicone) and to make it very simple for the operator to identify and repair it.

In addition to the control operated by the electronic control unit 24 or in place of the control operated by the electronic control unit 24, the ratios between the above linear speeds "V1", "V2", "V3" can be set mechanically by choosing appropriate dimensions for the unwinding rollers 16, the first roller and the second roller 21, 22 of the control device 21 and the pair of counter-rotating rollers 17.

In a further embodiment, not illustrated in detail in the accompanying figures, a first load cell is located just downstream of the reel 6 of elastic thread and is operatively coupled to each elastic thread 5 to measure a tension correlated to the first percentage elongation and a second load cell is located just downstream of the control device 21 and operatively coupled to each elastic thread 5 to measure a tension correlated to the second percentage elongation. The electronic control unit 24 is configured and/or programmed to adjust the first linear speed V1 of the motorized unwinding rollers 16 and/or the second linear speed V2 of the motorized transport surface according to the tensions detected by the load cells, so as to give each elastic thread 5 said first percentage elongation and said second percentage elongation.

A device for signaling 25 the breakage of the threads 5 is operatively positioned between the control device 21 and the pair of counter-rotating rollers 17, i.e. where the threads 5 are most likely to break.

The device for signaling 25 comprises: a support body 26 constrainable to a frame of the plant 1 and a series/set/plurality of rocker arms 27 mounted on the support body 26, mutually juxtaposed and oscillating about a common axis "J". In the illustrated embodiment, the rocker arms 27 are twenty-five, as many as the threads 5 fed in parallel.

The support body 26 comprises a base and two side walls 28 mounted on the base and mutually parallel and spaced apart. A shaft 29 extends orthogonal to the two side walls 28 and has opposite ends connected to said side walls 28. The shaft 29 is fixed with respect to said side walls 28. The rocker arms 27 are pivoted on the shaft 29 so as to be able to oscillate independently of each other, with respect to the shaft 29 and around the common axis "J" (which is the main axis of the shaft 29) and they are placed side by side to form a set.

Each of the rocker arms 27 has a flattened shape and extends orthogonal to the shaft 29. Each of the rocker arms 27 comprises a head end 30, configured to come into contact with a respective stretched thread 5 passing over said rocker arms 27, and a tail end 31 opposite the head end 30. In the illustrated embodiment, each of the rocker arms 27 has an L-shaped shape. The longer section of the L is crossed by the shaft 29 and has the tail end 31. The shortest section of the L is facing upwards and defines the head end 30.

The head end 30 of each rocker arm 27 has a groove 32 or notch open upwards and configured to receive a section of a respective thread 5 and to act as a guide for the thread 5.

A distance between median lines of two adjacent head ends 30 is equal to the distance between two adjacent threads 5 and is for example equal to about 10 mm. The device for signaling 25 comprises a first bar 33 mounted on the support frame 26 and below the head ends 30 of the series of rocker arms 27. The first bar 33 extends orthogonal to the two side walls 28 and has opposite ends connected to said side walls 28. The first bar 30 is fixed with respect to said side walls 28. The signaling device 25 comprises a second bar 34 mounted on the support frame 26 and below the tail ends 31 of the series of rocker arms 27. The second bar 34 extends orthogonal to the two side walls 28 and has opposite ends connected to said side walls 28. The second bar 34 is fixed with respect to said side walls 28.

The shaft 29, the first bar 33 and the second bar 34 are connected to or are part of an electrical circuit, possibly connected to the electronic control unit 24. For example, the electrical circuit is formed by the shaft 29, the second bar 34 and each rocker arm 27. The rocker arms 27 are electrically in contact with the shaft 29. The shaft 29, the first bar 33 and the second bar 34 are electrically isolated from the whole structure of the plant 1. The shaft 33 is isolated and without any electrical connection.

The first bar 33 and the second bar 34 also perform a limit stop function for the rocker arms 27 which are free to oscillate around the shaft 29.

In particular, each of the rocker arms 27 can oscillate, independently of the others, between a first position, in which the head end 30 is lowered by the action of the stretched thread 5 placed in the groove 32 of said head end 30, and a second position, in which the head end 30 is raised in the absence of said stretched thread 5 and under the action of the weight of the rocker arm 27 itself. The weight acts on a center of mass of the rocker arm 27 placed between the common axis "J" and the tail end 31. The distribution of the mass of each rocker arm 27 is in fact such as to carry and maintain said rocker arm 27 in the second position in the absence of the stretched thread 5 acting on the head end 30.

In the first position (FIG. 4), the rocker arm 27 rests against the first bar 33, the circuit is open and the plant 1 operates. In the second position (FIG. 5), the rocker arm 27 rotates by gravity and rests against the second bar 34, thus closing the electric circuit between the shaft 29, the rocker arm 27 and the shaft 34 and thus stopping the plant 1 or at least part thereof.

More in detail, in the normal operating condition of the plant 1, when all the elastic threads 5 are present and intact, all the rocker arms 27 are held in the respective first positions by the threads 5 themselves, as shown in FIGS. 2 and 4.

If and when a thread 5 breaks, the respective rocker arm 27 moves rotating to the second position, closing the electric circuit. Such a contact triggers a signal to stop the plant 1, or at least part of said plant 1, and possibly also an alarm signal, for example sound and/or visual. The signaling device 25 therefore also constitutes an automatic safety system to the plant 1.

The operator, looking at the signaling device 25, can immediately realize which thread 5 has broken because the respective rocker arm 27 is in the second position, with the head end 30 protruding upwards and is capable of repairing it and placing it in the groove 32 bringing the rocker arm back to the first position.

If the threads 5 are less in number than the rocker arms 27, the unused rocker arms 27 are arranged in the second position but are made electrically inactive by placing a ring of insulating material, for example polymeric, between the tail end 31 of each of said inactive rocker arms 27 and the second bar 34.

Figure 8:
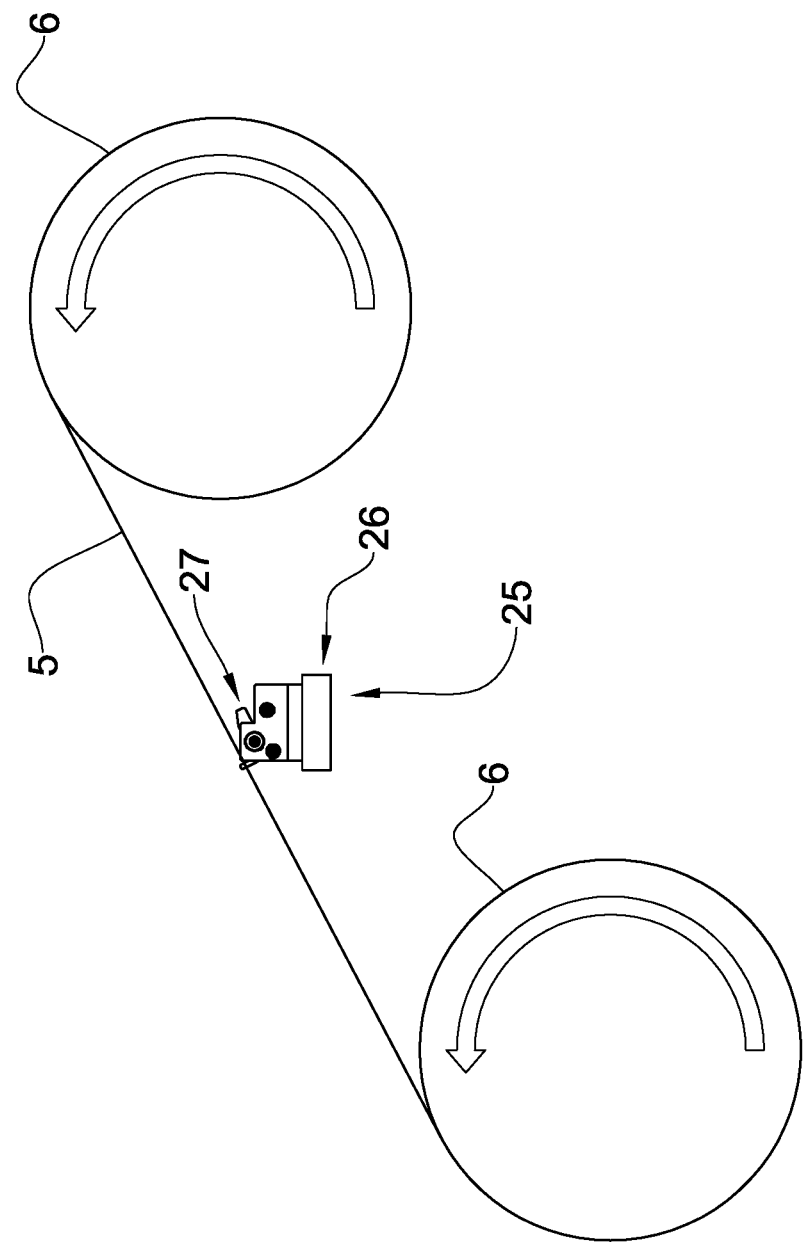
FIG. 8 is a schematic lateral view of a different embodiment of a device for feeding threads.

The signaling device 25 described can also be used in other types of plant in which a plurality of threads are fed in parallel, such as for example a plant for the production of the threads themselves. In FIG. 8, the signaling device 25 is placed between two arrays of reels. A first array of reels 5 from which the threads 5 are unwound and a second array of reels 6 on which the threads 5 are wound. The signaling device 25 is placed between the two arrays and along the path of said threads 5, more or less elastic.

ELEMENTS

1 Plant for the production of layered composite articles
2 Layered composite article
3 Web material
4 Reel of web material
5 Thread
6 Thread reel
7 First sector of the plant
8 Continuous semi-finished product
9 Second sector of the plant
10 Third sector of the plant
11 Fourth sector of the plant
12 Reel holder for reel of web materials
13 Reel holder for thread reel
14 Elastic semi-finished web product
15 Device for feeding elastic threads
16 Motorized unwinding roller
17 Pair of counter-rotating rollers
18 Main roller of the pair of counter-rotating rollers
19 Auxiliary roller of the pair of counter-rotating rollers
20 Glue dispenser
21 Control device
22 First roller of the control device
23 Second roller of the control device
24 Electronic control unit
25 Thread breakage signaling device
26 Support body
27 Rocker arms
28 Side walls
29 Shaft
30 Head end
31 Tail end
32 Groove
33 First bar
34 Second bar
F Transport direction
X First axis of the main roller
Y Second axis of the auxiliary roller
Z First axis of the first roller
K Second axis of the second roller
J Common axis of rocker arms
V1 First linear speed
V2 Second linear speed
V3 Third linear speed

The invention claimed is:

1. Method for feeding elastic threads in a process for the production of layered composite articles, comprising: feeding at least one elastic thread along a path extending from a reel of said elastic thread up to a joining zone with at least one web material;
wherein feeding said at least one elastic thread along said path comprises:
giving said at least one elastic thread a first percentage elongation along a first section of said path extending between the reel and a control zone;
giving said at least one elastic thread a second percentage elongation along a second section of said path extending between the control zone and the joining zone;
wherein the second percentage elongation is greater than the first percentage elongation and a length of the first section is greater than a length of the second section.

2. Method according to claim 1, wherein a ratio between the first percentage elongation and the second percentage elongation is greater than or equal to 0.1 and less than or equal to 0.9.

3. Method according to claim 1, wherein a ratio between the first percentage elongation and a percentage elongation at break of said elastic thread is less than 0.8.

4. Method according to claim 1, wherein a ratio between the length of the second section and the length of the first section is greater than or equal to 0.02 and less than or equal to 0.5.

5. Method according to claim 1, wherein the length of the second section is less than 1 m.

6. Method according to claim 1, wherein the length of the first section is greater than 2 m.

7. Method according to claim 1, wherein the layered composite articles are sanitary articles, selected from the group comprising: sanitary napkins, diapers, diapers for adults, panty liners; wherein it is provided to feed a plurality of elastic threads.

8. Device for feeding elastic threads in a plant for the production of layered composite articles, comprising:
at least one reel holder for at least one elastic thread wound in a reel and at least one motorized unwinding roll associated with the reel holder;
a pair of opposed transport surfaces configured to receive together and to join at least one web material with said at least one elastic thread unrolled from the reel;
a control device comprising at least one motorized transport surface; wherein the motorized transport surface is operatively arranged between the motorized unwinding roll and the pair of opposed transport surfaces to act on the elastic thread extending between the motorized unwinding roller and the pair of opposed transport surfaces;
wherein the control device is configured and/or programmed to adjust a linear speed of the motorized transport surface so as to give said at least one elastic thread a first percentage elongation, between the motorized unwinding roller and the control device, less than a second percentage elongation, between the control device and the pair of opposed transport surfaces;
wherein the device is configured to define a path for the elastic thread extending between the reel holder and the pair of opposed transport surfaces;
wherein a first section of said path extending between the reel holder and the control device is greater than a second section of said path extending between the control device and the pair of opposed transport surfaces.

9. Device according to claim 8, wherein a ratio between the length of the second section and the length of the first section is greater than or equal to 0.02 and less than or equal to 0.5.

10. Device according to claim 8, wherein the length of the second section is less than 1 m.

11. Device according to claim 8, wherein the length of the first section is greater than 2 m.

12. Device according to claim 8, wherein the control devices comprises a first roller and a second roller having reciprocally coupled peripheral surfaces and defining said at least one motorized transport surface; wherein at least one of said first roller and second roller is motorized.

13. Device according to claim 12, wherein the peripheral surface of the first roller is metallic and the peripheral surface of the second roller is made of rubber or vice versa.

14. Plant for the production of layered composite articles, comprising at least one device for feeding elastic threads according to claim 8.

\* \* \* \* \*